(12) United States Patent
Barker

(10) Patent No.: US 6,663,556 B2
(45) Date of Patent: Dec. 16, 2003

(54) STIMULATORS AND STIMULATING COILS FOR MAGNETICALLY STIMULATING NEURO-MUSCULAR TISSUE

(75) Inventor: Anthony T Barker, Sheffield (GB)

(73) Assignee: The Magstim Company Limited, Dyfed (GB)

( * ) Notice: Subject to any disclaimer, the term of this patent is extended or adjusted under 35 U.S.C. 154(b) by 62 days.

(21) Appl. No.: 09/803,008

(22) Filed: Mar. 12, 2001

(65) Prior Publication Data

US 2002/0128533 A1 Sep. 12, 2002

(51) Int. Cl.[7] ................................................ A61N 2/00
(52) U.S. Cl. ......................... 600/14; 335/301; 335/209
(58) Field of Search .......................... 600/13–15, 9–12; 335/301, 302–306, 209; 324/318

(56) References Cited

U.S. PATENT DOCUMENTS

| | | | | |
|---|---|---|---|---|
| 946,193 A | * | 1/1910 | Bachelet | 335/301 |
| 2,988,806 A | * | 6/1961 | Adams et al. | 75/246 |
| 3,427,156 A | * | 2/1969 | Reinstadler | 419/23 |
| 3,467,076 A | * | 9/1969 | Frisch et al. | 335/301 |
| 4,818,966 A | * | 4/1989 | Miyamoto et al. | 335/296 |
| 4,998,976 A | * | 3/1991 | Rapoport | 128/653.5 |
| 5,766,124 A | * | 6/1998 | Polson | 600/13 |
| 5,774,034 A | * | 6/1998 | Yoneda et al. | 335/301 |
| 6,179,770 B1 | * | 1/2001 | Mould | 600/13 |
| 6,231,497 B1 | * | 5/2001 | Souder | 600/9 |

FOREIGN PATENT DOCUMENTS

| | | |
|---|---|---|
| EP | 39206 | 11/1981 |
| EP | 252594 | 1/1988 |
| GB | 2264642 | 9/1993 |
| GB | 2271931 | 5/1994 |
| RU | 2062626 | * 6/1996 |
| SU | 1641360 | 6/1988 |

* cited by examiner

Primary Examiner—John A. Jeffery
(74) Attorney, Agent, or Firm—Nixon & Vanderhye, PC

(57) ABSTRACT

A stimulating coil for use in apparatus for the magnetic stimulation of neuro-muscular tissue. having a ferromagnetic back disposed adjacent one broad side of the coil. the material of the ferromagnetic back exhibiting high permeability and high resistivity.

2 Claims, 2 Drawing Sheets

STIMULATORS AND STIMULATING COILS FOR MAGNETICALLY STIMULATING NEURO-MUSCULAR TISSUE

FIELD OF THE INVENTION

The present invention relates to stimulators including stimulating coils constructed and intended for the magnetic stimulation of neuro-muscular tissue by inducing electric currents in such tissue

BACKGROUND OF THE INVENTION

Stimulating apparatus of the kind mentioned commonly includes means for applying at least one current pulse and preferably a series of current pulses to a coil, which may be a simple circular coil, or a figure of eight coil or be a coil with a plurality of turns forming the pulse generating apparatus for use with such a coil is well known and is described for example in GB Patent number 2298370 and European Patent EP-0692993.

It is customary practice to wind stimulating coils as a single layer on or in a non magnetic support so that all the coil can be disposed as closely as possible to the tissue that is to be stimulated. The coil is in essence apart from any insulating coating which is normally required owing to the high voltages and currents disposed in air, so that the magnetic field produced when current flows through the coil is all in a region of high reluctance.

SUMMARY OF THE INVENTION

The present invention is based on the provision of a body of ferromagnetic material, preferably highly permeable low reluctance material, disposed adjacent one broad side of the coil, i.e. the rear of the coil The material of the body is preferably selected to provide a highly permeable block with low eddy current loss, and may comprise sintered iron powder.

Reference will be made hereinafter to the accompanying drawings, in which

DESCRIPTION OF A PREFERRED EMBODIMENT

Figure 1:
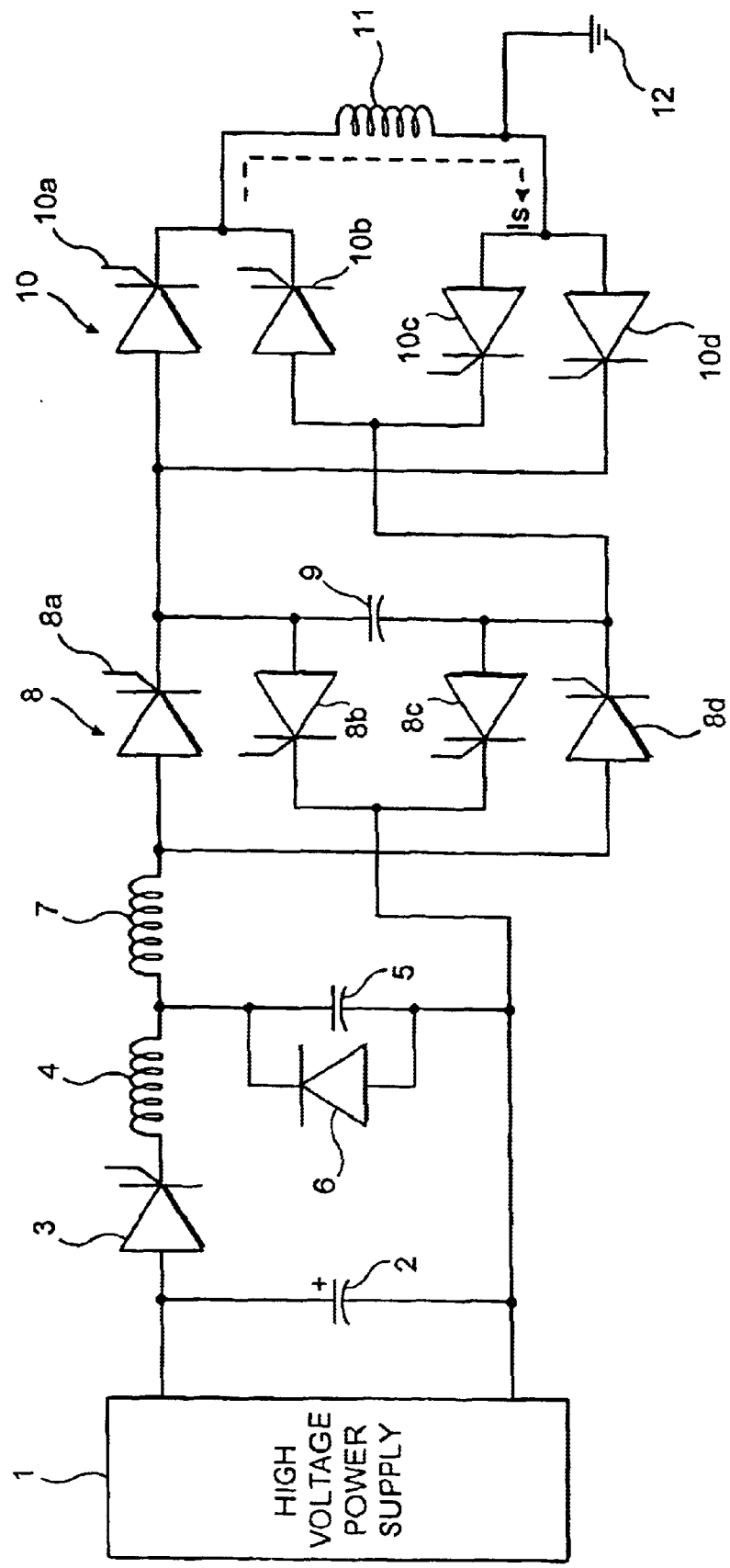
FIG. 1 is a schematic drawing of a magnetic stimulator.

FIG. 1 illustrates for the sake of completeness a known form of magnetic stimulator which produces a pulse or a series of pulses through a magnetic coil known as the stimulating coil, for use in the stimulation of neuro-muscular tissue. The time-varying magnetic field, having a maximum value typically up to several Teslas, induces electric currents in the tissue Neuro-muscular stimulation is an established form of therapy.

The stimulator shown in FIG. 1 corresponds to one embodiment described in U.S. Pat. No. 5,766,124 issued Jun. 30, 1998 to Polson and commonly assigned herewith. It is based on the accumulation of charge by a reservoir capacitor, the pumping of charge from this reservoir capacitor to a transfer capacitor and a charge pump for transferring charge from this transfer capacitor to a "discharge" capacitor. The switching circuit associated with the discharge capacitor can operate substantially independently of the rate of charging of the reservoir capacitor.

More particularly a high voltage power supply 1 provides a charging current to reservoir capacitor 2. Conduction of a controlled rectifier 3 in circuit with an inductor 4 transfers charge from the capacitor to a transfer capacitor 5. A free wheeling diode 6 is disposed in parallel with the capacitor 5 to conduct reverse current generated when the rectifier 3 is turned off. Charge may be transferred from the transfer capacitor 5 to a discharge capacitor 9 by means of a controlled rectifier circuit 8 which comprises controlled rectifiers 8a to 8d. Capacitor 9 is controllably discharged by means of rectifier circuit 10, composed of controlled rectifiers 10a to 10d, into a stimulating coil 11 normally provided with an earth connection 12.

Figure 2:
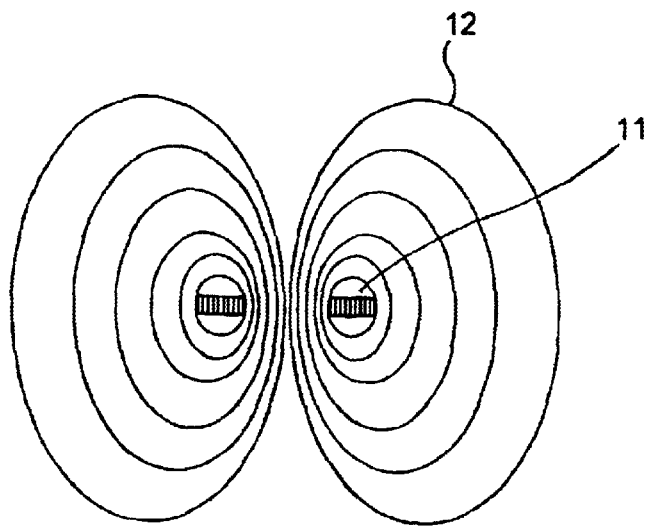
FIG. 2 is an illustration of a stimulating coil and its magnetic field.

As previously mentioned, the stimulating coils are normally wound as a single layer on or in a non-magnetic support, so that all the conductors can be as close as possible to the tissue which is to be stimulated FIG. 2 shows a cross section of a typical coil 11 and the magnetic field lines 12 associated with it. The magnetic field lines are symmetrical about both the axis and the plane of the coil windings.

Figure 3:
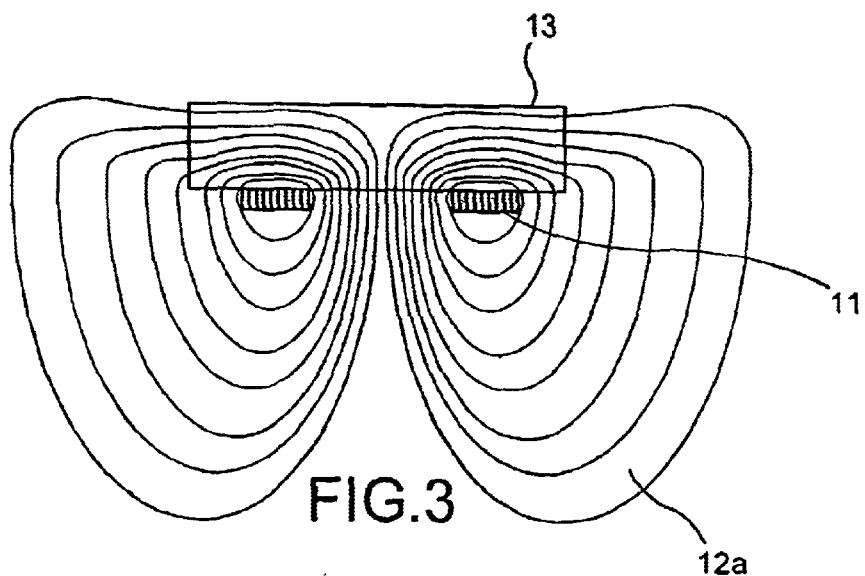
FIG. 3 is a drawing of a stimulating coil provided with a magnetic back according to the invention.

If a member of ferromagnetic material is placed behind the coil, shown in FIG. 3, the magnetic field is distorted and in particular is now asymmetric about the plane of the coil The effect of the ferromagnetic material is preferably to provide a low reluctance path for the magnetic field at the back of the coil. Very little of the energy supplied by the magnetic stimulator need be used to drive the magnetic field at the back of the coil so that the bulk of the energy supplied to the coil may be employed to establish the magnetic field on the other side of the coil. The end result is that for the same supplied energy the magnetic field strength is higher in the patient's tissue.

FIG. 3 illustrates a coil 11 with a magnetic back 13 disposed so that substantially all the coil can be brought into close proximity with a patient but the region at the back of the coil is occupied by ferromagnetic material, which is preferably highly permeable with low eddy current loss.

Figure 4:
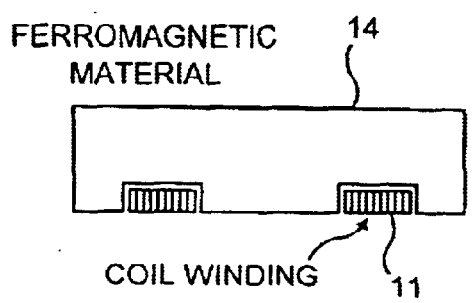
FIG. 4 is drawing of another embodiment of a stimulated coil provided with a magnetic back according to the invention.

FIG. 4 illustrates a slightly different arrangement in which the coil 11 is disposed in slots in one broad face of the body 14 of ferromagnetic material.

Other configurations are possible. The ferromagnetic body may be extended or chamfered to provide a bowl like shape. The whole of the patient's side of the structure could be bowl shaped and accommodate a slightly recessed pancake coil. The coil may be in a figure of eight form disposed closely adjacent the body of ferromagnetic material.

The optimum choice for the ferromagnetic material of the body is not necessarily straight forward, because many ferromagnetic materials have quite high electrical conductivity. If a homogeneous member of such a material were used, there would be power loss in eddy currents induced within the ferromagnetic core and those eddy currents could nullify any efficiency gain obtained by lowering the reluctance of the magnetic circuit. The traditional method of reducing eddy currents, in other contexts, is to form a magnetic core from a multiplicity of laminations. In the present case the laminations would have to be arranged radially, which is not particularly convenient.

Preferably therefore the material of body 13 or 14 is composed of a compressed and sintered powder. The powder may be substantially pure iron but could be another material which in the preferred form has a high permeability (for example 500 relative to air). The preferred material for the core is a soft magnetic composite powder such as that sold as "Somaloy", available from Hoganas.

Other materials may be employed. Preferably the permeability is at least 10 and the bulk resistivity should be such that for a stimulating frequency of 50 Hz, and a mark:space ratio of 1:80 the eddy current loss is of the order of 12.5 watts per kilogram.

The provision of a magnetic back for a coil in accordance with the invention does not require any significant redesign of the coil. The back may be disposed adjacent the rear side of presently known coils.

The cross sectional area of the ferromagnetic back is not constrained by the size of the coil, as would be the case if the coil were wound round the ferromagnetic core. The thickness of the member can be increased as necessary to avoid attainment of saturation.

The presence of the ferromagnetic material increases the self inductance of the coil. For a given geometry this provides the opportunity to employ fewer turns in the coil with a larger cross sectional area. Thereby the electrical resistance of the coil may be reduced and that reduction reduces the loss of energy in the coil.

What is claimed is:

1. A magnetic stimulator for neuro-muscular tissue, comprising:
    a stimulating coil having a front and a rear;
    a storage capacitor;
    a circuit for repeatedly discharging said capacitor into said coil; and
    a ferromagnetic back disposed adjacent the rear of the coil so as to be at the back of the coil when the coil is disposed adjacent a patient,
    wherein said ferromagnetic back is a homogeneous member comprising sintered iron powder having a relative permeability greater than ten and a high bulk resistivity and said coil is disposed in recesses formed in a front portion of the ferromagnetic back.

2. A stimulator according to claim 1, wherein said ferromagnetic back has a bulk resistivity such that for a stimulating frequency of 50 Hertz and a mark to space ratio of 1:80 in a current through said coil, eddy current loss in said back is less than 15 watts per kilogram.

\* \* \* \* \*